United States Patent [19]

Dudkowski

[11] 4,150,969
[45] Apr. 24, 1979

[54] 2,6-DINITROANILINE HERBICIDAL COMPOSITIONS

[75] Inventor: Joseph J. Dudkowski, Bridgewater, N.J.

[73] Assignee: American Cyanamid Company, Stamford, Conn.

[21] Appl. No.: 865,541

[22] Filed: Dec. 29, 1977

Related U.S. Application Data

[63] Continuation-in-part of Ser. No. 780,377, Mar. 23, 1977, Pat. No. 4,082,537.

[51] Int. Cl.² ............................................. A01N 17/00
[52] U.S. Cl. .................................. 71/121; 71/DIG. 1
[58] Field of Search ............................ 71/121, DIG. 1

[56] References Cited

U.S. PATENT DOCUMENTS 3,154,397  10/1964  Martin .............................. 71/DIG. 1
3,920,742  11/1975  Lutz et al. ............................... 71/121

Primary Examiner—Catherine L. Mills
Attorney, Agent, or Firm—H. G. Jackson

[57] ABSTRACT

The invention is a solid herbicidal composition comprising a molecular solution of ethoxylated β-diamines in 2,6-dinitroanilines. The solution of the surfactant in the 2,6-dinitroaniline prevents formation of large crystals of the herbicides when in wettable powder form.

7 Claims, No Drawings

2,6-DINITROANILINE HERBICIDAL COMPOSITIONS

This application is a continuation-in-part of Ser. No. 780,377, filed Mar. 23, 1977, now U.S. Pat. No. 4,082,537.

The broad spectrum herbicides of formula I, below, methods of preparation thereof, and their use as a highly effective preemergence herbicide for the control of undesirable plant species, are disclosed by A.W. Lutz et al. in U.S. Pat. No. 3,920,742 (1975).

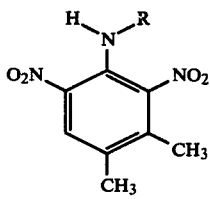

wherein R is 1-ethylbutyl, 1-ethylpropyl, 1-methylpropyl or 1-methylbutyl.

For use in agriculture, formula (I) herbicides may be advantageously formulated as a wettable powder. Wettable powders are usually prepared by grinding and milling the ingredient with a solid carrier, such as attaclay, kaolin, diatomaceous earth, synthetic calcium silicate, fullers earth, talc, pumice, and the like. Usually, about 25% to 75% by weight of the active material, and from about 75% to 25% by weight of solid carrier, is used. In addition, there is generally added about 1% to 5% by weight of a dispersing agent, such as alkali metal salts of naphthalene sulfonic acid and anionic-nonionic blends, and from about 1% to 5% by weight of a surfactant, such as polyoxyethylene alcohols, acids, adducts, sorbitan fatty acid esters, sorbital esters, and the like. The amount of solid carrier is then reduced accordingly to compensate for the amounts of dispersing agent(s) and surfactant(s) incorporated into the formulation.

Wettable powders are usually dispersed in water and applied as dilute aqueous sprays at a rate of 0.28 kg to 22.4 kg/hectare of active ingredient to the area where control of undesirable plant species is desired.

A typical wettable powder containing N-(1-ethylpropyl)-2,6-dinitro-3,4-xylidine is represented by the following compositions:

| Component | Percent by Weight |
|---|---|
| N-(1-ethylpropyl)-2,6-dinitro 3,4-xylidine | 75.0 |
| Sodium salt of condensed naphthalene sulfonic acid | 1.0 |
| Sodium N-methyl-N-oleoyltaurate | 5.0 |
| Synthetic calcium silicate (quantity sufficient to 100%) |  |
|  | 100.0 |

The above components are blended and jet-milled to yield a wettable powder, containing 75% by weight of active material.

When this and similar formulations were evaluated in the greenhouse and in field trials, it was noted that freshly prepared wettable powders dispersed well in water and gave excellent preemergence control of undesirable plant species, irrespective whether the wettable powder was prepared from purified (recrystallized) or technical grade N-(1-ethylpropyl)-2,6-dinitro-3,4-xylidine. When, however, these samples were stored at ambient temperature for a period of time of two to three months, the aqueous dispersions prepared from the same samples showed that the active material tended to settle out rapidly and gave uneven control over the area treated. Some of these samples caused blockage of screens in the spray equipment, necessitating the dismantling and cleaning of the equipment.

Microscopic examination of the aqueous dispersions prepared from freshly prepared and aged wettable powders indicated that in the freshly prepared powders the above-identified herbicide is present in the form of a yellow, microcrystalline solid; whereas, in the aged samples, the same compound is present in the form of large orange crystals, 150 to 200 um in size. These large crystals tend to settle out rapidly from the aqueous dispersions and may cause blockage of screens in spray equipment, and irregular distribution over the treated plots.

From the above data, it is surmised that the herbicide exists at ambient temperatures in the form of two distinct polymorphs: a yellow microcrystalline form and an orange macrocrystalline form; and that of the two, the latter appears to be the more stable polymorph. X-ray powder diffraction pattern data obtained on both types tends to confirm the above assumption. Apparently, in the course of the preparation of N-(1-ethylpropyl)-2,6-dinitro-3,4-xylidine, the yellow polymorph is obtained, which then slowly converts at ambient temperature to the more stable orange polymorph. Obviously, it would be of advantage if this conversion could be prevented, or at least slowed down considerably.

Surprisingly, we now find that if more than 1% to about 2% by weight of ethoxylated β-diamine is dissolved in molten N-(1-ethylpropyl)-2,6-dinitro-3,4-xylidine, the homogeneous melt is then cooled down until it solidifies, and is then used in the preparation of the aforesaid wettable powders; the thus-obtained wettable powders, when stored, show the absence of the orange polymorph and yield stable aqueous dispersions substantially free of large xylidine crystals which can cause blockages of screens in spray equipment. Ethoxylated β-diamines are compounds of the formula:

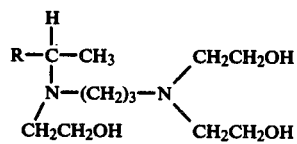

wherein R is $C_9$–$C_{20}$.

In general, a mixture of less than 99% to about 98% by weight of N-(1-ethylpropyl)-2,6-dinitro-3,4-xylidine and more than 1.0% to about 2% by weight of ethylated β-diamines is stirred and heated at 56°–60° C. until a homogeneous melt forms. The melt is then poured in shallow containers and allowed to cool and solidify. The solid is then ground, and the thus-obtained solid herbicide/surfactant molecular solution is used for the preparation of the aforesaid wettable powders.

I also find that 1% or less by weight of the surfactant ethoxylated β-diamines present in the herbicide will not prevent the transition of the yellow polymorph to the undesired orange polymorph.

It should be noted that if more than 1% to about 2.0% by weight of ethoxylated β-diamines is simply added during the preparation of wettable formulations (i.e., it is mechanically blended with the other components), it will not prevent the formation of the undesirable orange polymorph. However, when the same amount of ethoxylated β-diamines is melted together with the xylidine and a molecular solution is formed between the two formation of the undesirable polymorph is prevented.

The invention is further illustrated by the following non-limiting examples, below.

EXAMPLE 1

Preparation of Experimental Wettable Powders from N-(1-Ethylpropyl)-2,6-dinitro-3,4-xylidine, which has been fused with ethoxylated β-diamines Procedure:

A mixture of N-(1-ethylpropyl)-2,6-dinitro-3,4-xylidine (99.0 g) and ethoxylated β-diamines (1.0 g) is stirred and heated until completely liquified. The melt is stirred for 15 minutes and then allowed to cool and solidify, By the above procedure, the following samples are prepared as shown in Table I below.

TABLE I

| Component | Experimental Wettable Powders | | |
|---|---|---|---|
| | 1 | 2 | 3 |
| N-(1-ethylpropyl)-2,6-dinitro-3,4-xylidine (Technical Grade) | | | |
| a. (92.3% real) | 99.0 | | |
| b. (92.8% real) | | 99.0 | |
| C. (91.4% real) | | | 99.0 |
| Ethoxylated β-diamines (100% real) | 1.0 | 1.0 | 1.0 |
| Total weight in grams | 100.0 | 100.0 | 100.0 |
| Percent real | 91.4 | 91.4 | 90.5 |

Preparation of 75% wettable powders from the above samples.

Procedure:

The components of the blends are thoroughly mixed and are then jet-milled. In Table II, below, the composition of the wettable powders prepared is given.

TABLE II

| Composition of Wettable Powders Containing 75% by Weight of N-(1-Ethylpropyl)-2,6-dinitro-3,4-xylidine | | | |
|---|---|---|---|
| | Wettable Powders 75% Real | | |
| Component | A | B | C |
| Table I. Sample 1. (91.4% real) | 41.0 | | |
| Table I. Sample 2. (91.4% real) | | 40.8 | |
| Table I. Sample 3 (90.5% real) | | | 41.4 |
| Sodium salt of condensed naphthalene sulfonic acid | 0.5 | 0.5 | 0.5 |
| Sodium N-methyl-N-oleoyltaurate | 2.5 | 2.5 | 2.5 |
| Synthetic calcium silicate | 6.0 | 6.2 | 5.6 |
| Total weight in grams | 50.0 | 50.0 | 50.0 |

The above prepared blends are examined by mixing 1.0 g of each with 99 ml of tap water in a 100 ml graduate cylinder, determining the time needed to fully wet out the powders and observing the aqueous dispersions obtained. The blends are then stored at ambient temperature. At two and five months storage, aqueous dispersions are prepared from each sample by the procedure described above, and the dispersions are examined under a microscope at 660X for the presence or absence of the undesirable, large, orange crystals.

EXAMPLE 2

Evaluation of the Effect of Various Surfactants for the Prevention of the Formation of the Orange Polymorph in Wettable Powders Containing 75% by Weight of N-(1-ethylpropyl)-2,6-dinitro-3,4-xylidine.

Procedure:

Samples of N-(1-ethylpropyl)-2,6-dinitro-3,4-xylidine (92% real, 100 g each) are mixed with a surfactant (1% to 2% by weight, respectively) selected from those listed below; each mix is melted, is stirred a few minutes while molten, poured into shallow aluminum trays to cool and solidify. The thus-prepared samples are then used to prepare wettable powders by the procedure of Example 1, and having the composition as given in Table II of Example 1.

The following surfactants are evaluated:
a. Sodium dihexyl sulfosuccinate;
b. Tall oil ethoxylate;
c. Sodium diisopropyl naphthalene sulfonate;
d. Ethoxylated alkyl phenols;
e. Polyvinyl pyrrolidine (Average molecular weight: 10,000);
f. Nonylphenoxypoly(ethyleneethoxy)ethanol;
g. Dodecylphenoxypoly(ethyleneethoxy)ethanol;
h. Dialkylphenoxypoly(ethyleneethoxy)ethanol;
i. Octylphenoxypoly(ethyleneethoxy)ethanol;
j. Isopropyl myristate, melting point ∼3° C.;
k. Ethoxylated β-diamines; and
l. Ethoxylated β-amines.

The thus-prepared wettable powders are stored for three months at ambient temperatures, then dispersions (1.0 g sample in 99 ml water) are made of each and examined under a microscope at 660X for the presence or absence of large orange crystals. The data obtained are summarized in Table III below.

TABLE III

| Surfactant in Blends | Presence of Large Orange Crystals at Surfactant Concentration of | |
|---|---|---|
| | 1% | 2% |
| Control | yes | |
| a | yes | no |
| b | yes | yes |
| c | yes | yes |
| d | yes | yes |
| e | yes | yes |
| f | yes | yes |
| g | yes | yes |
| h | yes | yes |
| i | yes | yes |
| j | yes | yes |
| k | yes | no |
| l | yes | yes |

Results comparable to those in the Examples and Tables above are obtained with other 2,6-dinitroanilines of the invention.

I claim:

1. A solid herbicidal composition comprising a molecular solution of a surfactant of ethoxylated β-diamines of the formula

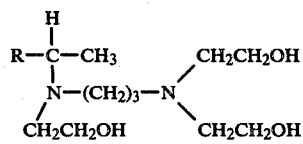

wherein R is $C_9$–$C_{20}$ in an amount effective to prevent crystallization of the herbicide and a herbicidal compound of the formula

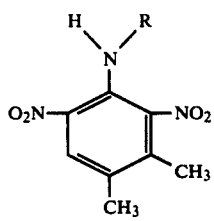

wherein R is 1-ethylbutyl, 1-ethylpropyl, 1-methylpropyl or 1-methylbutyl.

2. A composition according to claim 1 comprising a solution of more than 1.0% to about 2.0% by weight of ethoxylated β-diamine and less than 99.0% to about 98% by weight of N-(1-ethylpropyl)-2,6-dinitro-3,4-xylidine.

3. A wettable powder herbicidal composition comprising from about 25% to about 75% of a solid solution of a surfactant of ethoxylated β-diamines of the formula

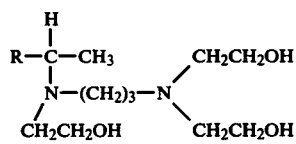

wherein R is $C_9$–$C_{20}$ in an amount effective to prevent crystallization of the herbicide and a herbicidal compound of the formula

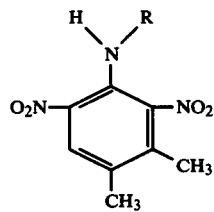

wherein R is 1-ethylbutyl, 1-ethylpropyl, 1-methylpropyl or 1-methylbutyl and from about 75% to about 25% of a solid carrier.

4. A herbicidal composition according to claim 3 wherein the herbicide is N-(1-ethylpropyl)-2,6-dinitro-3,4-xylidine.

5. A herbicidal composition according to claim 4 wherein the solution comprises more than 1.0% to about 2.0% by weight of ethoxylated β-diamine and less than 99.0% to about 98.0% by weight of N-(1-ethylpropyl)-2,6-dinitro-3,4-xylidine.

6. A method of preventing the formation of crystals in wettable powder formulations of compounds of the formula

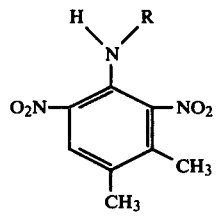

wherein R is 1-ethylbutyl, 1-ethylpropyl, 1-methylpropyl or 1-methylbutyl which comprises
melting the compound at about its melting point,
adding a surfactant of ethoxylated β-diamines of the formula

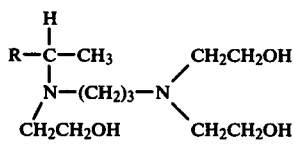

wherein R is $C_9$–$C_{20}$ in an amount effective to prevent crystallization of the dinitroaniline,
stirring the mixture until a homogeneous solution results, and then
cooling the melt until it resolidifies.

7. A method of preventing the formation of crystals in wettable powder formulations of N-(1-ethylpropyl)-2,6-dinitro-3,4-xylidine according to claim 6 wherein 99% to about 98.5% by weight of N-(1-ethylpropyl)-2,6-dinitro-3,4-xylidine is melted at 56°–60° C. and more than 1% to about 2.0% by weight of ethoxylated β-diamine is added to the melt and the mixture is stirred at about 56°–60° C. for a sufficient period of time to obtain a homogeneous solution.

* * * * *